(12) United States Patent
Boatner et al.

(10) Patent No.: US 8,475,369 B2
(45) Date of Patent: Jul. 2, 2013

(54) INTEGRATED PRESSURE AND TEMPERATURE CANNULA

(75) Inventors: Paul Boatner, Stevensville, MD (US); Scott Cardozo, Richmond, VA (US)

(73) Assignee: Ambu A/S, Ballerup (DK)

( * ) Notice: Subject to any disclaimer, the term of this patent is extended or adjusted under 35 U.S.C. 154(b) by 1095 days.

(21) Appl. No.: 12/453,180

(22) Filed: Apr. 30, 2009

(65) Prior Publication Data

US 2009/0299158 A1 Dec. 3, 2009

Related U.S. Application Data

(60) Provisional application No. 61/049,060, filed on Apr. 30, 2008.

(51) Int. Cl.
*A61B 5/01* (2006.01)
*A61B 5/08* (2006.01)
*A61M 15/00* (2006.01)

(52) U.S. Cl.
USPC ..................................... 600/301; 128/200.24

(58) Field of Classification Search
None
See application file for complete search history.

(56) References Cited

U.S. PATENT DOCUMENTS

| | | | |
|---|---|---|---|
| 4,686,975 A | 8/1987 | Naimon et al. | |
| 5,069,222 A | 12/1991 | McDonald | |
| 5,477,582 A * | 12/1995 | Yamashita | 15/231 |
| 6,155,986 A | 12/2000 | Brydon et al. | |
| 6,165,133 A | 12/2000 | Rapoport et al. | |
| 6,840,907 B1 * | 1/2005 | Brydon | 600/534 |
| 7,337,780 B2 * | 3/2008 | Curti et al. | 128/207.18 |
| 2003/0199780 A1 * | 10/2003 | Page | 600/538 |

* cited by examiner

*Primary Examiner* — Ernst Arnold
(74) *Attorney, Agent, or Firm* — Levy & Grandinetti

(57) ABSTRACT

The invention is an integrated thermal and pressure device and method for detecting breathing patterns. The device has a manifold, two parallel nasal cannulas stemming from the manifold, and at least one flexible tube. The flexible tube stems from the manifold and provides an airtight connection with the manifold and a pressure transducer apparatus. The device also includes at least a first temperature sensor for detecting temperatures of air flowing from one cannula to the other cannula. The device can include a second temperature sensor for sensing oral air flow temperatures.

6 Claims, 5 Drawing Sheets

INTEGRATED PRESSURE AND TEMPERATURE CANNULA

We claim the benefit under Title 35, United States Code, §119, of U.S. Provisional Application No. 61/049,060, filed Apr. 30, 2008, entitled CANNULA/THERM COMBINATION THERMULA, CANNUTHERM, CTHERM, PRESSUTHEMP, PRESSUTHERM DIAGNOSTIC DEVICE.

BACKGROUND OF THE INVENTION

1. Field of the Invention

The invention relates to cannulas for study of patients during sleep and monitoring their vital signs. Specifically, the invention relates to integrated cannulas that support sensors for monitoring a patient's vital signs including temperature and respiration pressure.

2. Description of Related Art

A cannula is a thin tube inserted into a body cavity. Certain cannulas are used to insert into a patient's nostrils to provide assisted respiration to the patient. Typically, respiratory cannulas are used to deliver oxygen to a patient.

The respiration of patients has become more sophisticated and often includes the monitoring of vital signs such as temperature and respiration pressure. The monitoring of these vital signs can permit an electronic device to detect irregularities in a patient's breathing. Apnea is one such irregularity wherein the patient's breathing stops. The electronic device can "alert" medical personnel through an alarm or other signal as to the irregularity or disruption in the patient's breathing.

Sophisticated electronic monitoring devices require sensors placed at exact points in the path of the patient's respiration. A failure to place the sensor correctly or to hold it firmly in place jeopardizes the reliability of the monitoring and subsequent alarms. Further, the more sensors that are held at critical locations for monitoring vital signs, the more awkward and uncomfortable the device is for the patient.

The industry has combined sensors and cannulas. These combinations tend to be limited in the vital signs that can be monitored or cumbersome for the patient.

U.S. Pat. No. 4,686,975 to Naimon et al. describes an electronic respirable gas delivery device. The invention includes a respiration sensor where a nasal cannula is connected via tubing to a sensitive pressure transducer with an amplifier for transforming the gas flow, depending upon pressure variations at the nasal cannula prongs, into an electrical signal for diagnostic information concerning the breathing pattern. The device does not provide any means for sensing oral breathing simultaneously with nasal breathing.

U.S. Pat. No. 5,069,222 to McDonald, Jr., describes a respiration sensor set. The invention includes a respiration sensor set with a pair of spaced-apart nasal temperature sensors and one oral temperature sensor. Support means hold the two nasal sensors in a spaced-apart condition and in parallel. The oral sensor is spaced apart in an axial alignment with one of the nasal sensors. This device provides only thermal indications of breathing and requires three temperature sensors. This device does not provide for a detector for respiration pressure.

U.S. Pat. No. 6,155,986 to Brydon et al. describes an apparatus for the monitoring of oro-nasal respiration. The device includes a respiration sensor system where a nasal cannula with two prongs is connected in parallel with the tubing from a third prong placed in the proximity of a patient's mouth. At the junction of the two tubes a single common tube is connected to a sensitive pressure transducer for monitoring oro-nasal respiration. The pneumatic impedances of the oral tube and the nasal tube are arranged to be different so that the contributions of respiratory flow from each of the tubes is substantially equal. The device uses only pressure sensing of breath flow which is unreliable at shallow breathing (low flow), and displacement of the prong in proximity to the mouth is very critical in order to provide a representative monitoring of mouth breathing.

U.S. Pat. No. 6,165,133 to Rapoport et al. describes an apparatus and method for monitoring breathing patterns. The device combines a respiration sensor system where a nasal cannula with two prongs has two temperature sensors attached to the nasal prongs and a third temperature sensor attached to an extension. The extension is oriented in the proximity of the patient's mouth. The two nasal temperature sensors are either attached to the outside of the prongs or just outside the opening of each prong. The device requires three temperature sensors and the position of the nasal sensors on the outside of the prongs can easily cause them to get in contact with secretion or be subject to fluid droplets which can cause the sensing of air temperature fluctuations to fail.

Diagnostic sleep studies or "polysomnograms" typically record parameters related to a patient's breathing in order to determine if a condition known as sleep apnea is present. Standard sensors include respiratory effort belts on the chest and abdomen, snore sensors or microphones on the neck, a body position sensor, and either thermal or pressure sensors to detect oral and/or nasal airflow. Thermal airflow detects a change in temperature between warm exhaled air and cooler room air that is inhaled. Thermal airflow is a good indicator of the presence or absence of breathing, but it does not measure the volume of airflow. Thermal airflow sensors are generally either a thermistor or a thermocouple but can be any sensor capable of detecting changes in airflow temperature.

The American Academy of Sleep Medicine ("AASM") recently revised its recommendations for sensor usage in accredited sleep labs. The AASM recommends that accredited sleep labs use a pressure transducer to detect hypopneas. Hypopneas occur when there is a greater than 50 percent reduction in breathing (as measured by volume of air exchanged) and a 10 second or greater cessation of breathing (as measured by a thermal sensor to detect apneas). This recommendation for the use of two different types of sensors has created a practical problem for polysomnographic technologists charged with preparing a patient for a sleep study and attaching the required sensors.

Both the thermal and pressure airflow sensors need to rest on the upper lip in order to sample the airflow from the patient's nasal and oral cavities. The presence of two separate sensors is often uncomfortable for the patient and difficult for the technologist to position properly.

The industry lacks an integrated cannula that provides for sensing nasal and/or oral breath temperatures and for sensing the pressure of the nasal breaths.

SUMMARY OF THE INVENTION

The invention is an integrated thermal and pressure device for detecting breathing patterns. The device includes a manifold, two parallel nasal cannulas stemming from the manifold, and at least one flexible tube. The flexible tube stems from the manifold and provides an airtight connection with the manifold and a pressure transducer apparatus. The device also includes at least a first temperature sensor for detecting temperatures of air flowing from one cannula to the other cannula. The device desirably includes a second temperature sensing device for sensing oral air flow temperatures.

The invention is also a method for detecting breathing patterns. The method includes a step of placing two parallel nasal cannulas stemming from a manifold into nasal passages of a patient. The sensing of nasal temperatures of air flowing from one cannula to the other cannula then occurs. The temperatures are sensed in the manifold between the two parallel nasal cannulas. Then, the sensing occurs of air pressures in the manifold through at least one flexible tube stemming from the manifold in an airtight connection with a pressure transducer apparatus. The sensing of oral air flow temperatures is performed with a second temperature sensor in contact with oral breathing of the patient.

DETAILED DESCRIPTION OF THE INVENTION

The Applicants created a device that combines a nasal or nasal/oral cannula with a reusable thermal sensor that integrates into the cannula and fits more comfortably on the patient. The device is easier for the technologist to position properly and provides both the pressure and thermal readings recommended by the AASM. The unique design of the reusable thermal sensor allows it to be positioned on the patient with only one lead wire rather than the standard configuration with wires that go back and across each side of the patient's face and hook behind the ears. In addition, when the thermal sensor is plugged into the cannula it effectively functions as a single unit that is easier to position and more comfortable than the common use of two separate sensors.

The invention is an integrated thermal and pressure device for detecting breathing patterns. The device includes a manifold, two parallel nasal cannulas stemming from the manifold, and at least one flexible tube. The flexible tube stems from the manifold and provides an airtight connection with the manifold and a pressure transducer apparatus. The device also includes at least a first temperature sensor for detecting temperatures of air flowing from one cannula to the other cannula. The device desirably includes a second temperature sensing device for sensing oral air flow temperatures. The device integrates a cannula and sensors that provide for sensing nasal and/or oral breath temperatures and for sensing the pressure of the nasal breaths.

Figure 1:
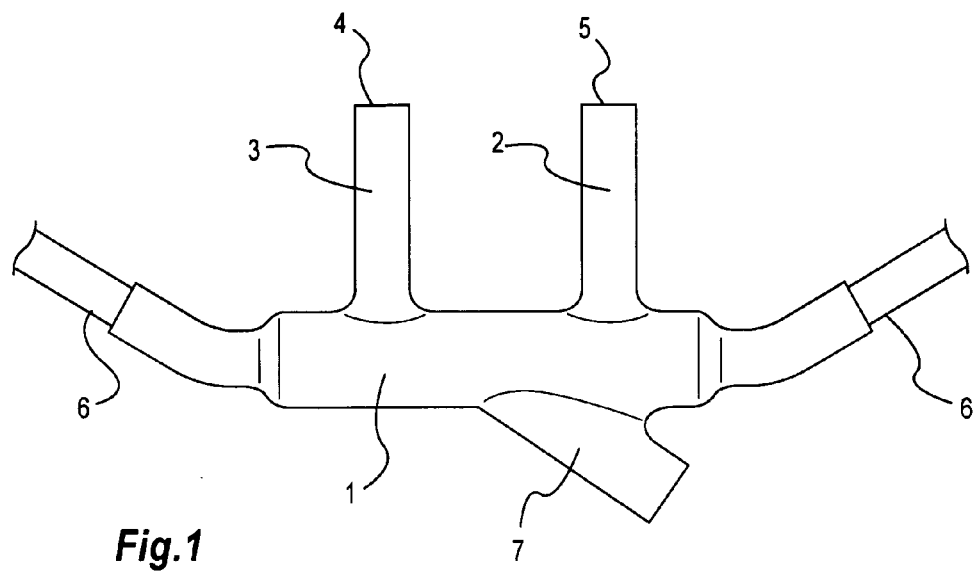
FIG. 1 illustrates a top plan view of the preferred embodiment of the invention including a manifold and two cannula.

FIG. 1 illustrates a top plan view of the preferred embodiment of the invention including a manifold 1 and two cannulas 2 and 3. The two cannulas 2 and 3 are preferably parallel or approximately parallel to one another. In alternative embodiments, the two cannulas 2 and 3 can converge slightly at their respective nasal ports 4 and 5. The slight convergence of the cannulas can assist holding the device in the nostrils of a patient.

The device of FIG. 1 is a preferred embodiment with a pressure conducting tube 6 extending from both sides of the manifold 1. These two pressure conducting tubes 6 can extend about the head of the patient, pass over the patient's ears, and unite in the back of the patient's head or neck. The pressure conducting tubes 6 can be separately connected or connected into a single tube (not shown) and form an airtight connection with a pressure transducer (not shown).

Alternatively, all or a portion of a pressure conducting tube can be replaced with a transducer and signal conductor. However, the preferred embodiment uses a pneumatic system wherein the transducer is separated from the immediate moisture of the patient's breath. Other embodiments can include a volumetric device (not shown) or other device for analyzing the characteristics of the patient's breath or breathing such as moisture and force.

The preferred embodiment of FIG. 1 illustrates a structure wherein the pressure conducting tubes 6 are molded into a single structure with the manifold 1. Alternative embodiments can include airtight fixtures to connect the pressure conducting tubes 6 to the manifold 1.

The invention includes at least one sensor port 7. The preferred embodiment has a cylindrical protrusion that provides a "female fitting" for a sensor. The sensor port 7 is desirably mounted at an angle from the patient's nose on the manifold 1. Inserting and removing a sensor at an angle from the patient's nose reduces the opportunity for injuring the patient and/or forcing the cannulas 2 and 3 too deeply into the nostrils.

Figure 2:
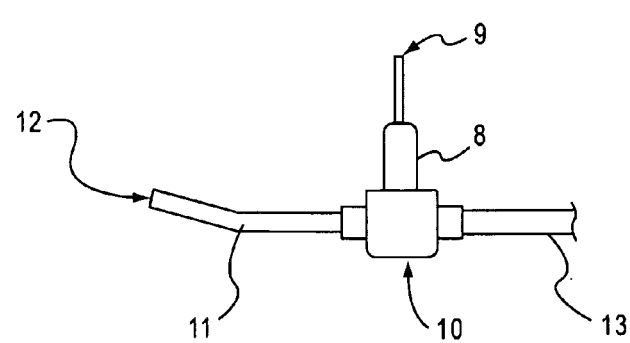
FIG. 2 illustrates a top plan view of the preferred embodiment of a first temperature sensor for nasal temperatures suitable for use with the manifold and cannula of the invention.

FIG. 2 illustrates a top plan view of the preferred embodiment of a first temperature sensor for sensing nasal temperatures suitable for use with the manifold 1 and cannulas 2 and 3 of the invention. The preferred first temperature sensor includes a sensor or sensor terminal 9. The sensor terminal 9 of the preferred embodiment detects temperatures and can be formed by a thermocouple, thermistor, or similar device.

The sensor terminal 9 in the preferred embodiment extends from a plug 8. The plug 8 complements the fitting or sensor port 7 on the manifold 1. These fittings in the preferred embodiment are airtight friction fittings but can include screw, tension-twist, or other fittings.

The base of the plug 8 is mounted in the preferred embodiment on a junction or knob 10. In the preferred embodiment, the knob 10 is a node wherein the sensor terminal 9 joins a signal transmitting line or, in the preferred embodiment, an electrical cable 13. The electrical cable 13 permits the signal, voltage, or other transmission from the sensor to a processor unit (not shown). In the preferred embodiment, the voltage from the sensor terminal 9 is carried by the electrical cable 13 to a processor that records the temperatures of the nasal air flow and can compare those temperatures to statistical norms, the patient's own temperature fluctuations over time, or other selected parameters.

The first temperature sensor of FIG. 2 is desirably combined with a second temperature sensor for sensing oral breathing temperatures. This second temperature sensor is formed in the preferred embodiment by a short flexible wire 11 and a terminal oral air flow thermal sensor 12. The flexible wire 11 can be formed by a structure of tape and microwire for attachment to a patient's lip. The oral air flow thermal sensor 12 of the preferred embodiment is a second thermocouple.

The second thermocouple is connected within the junction or knob 10 to the multi-wire electrical cable 13.

Figure 3:
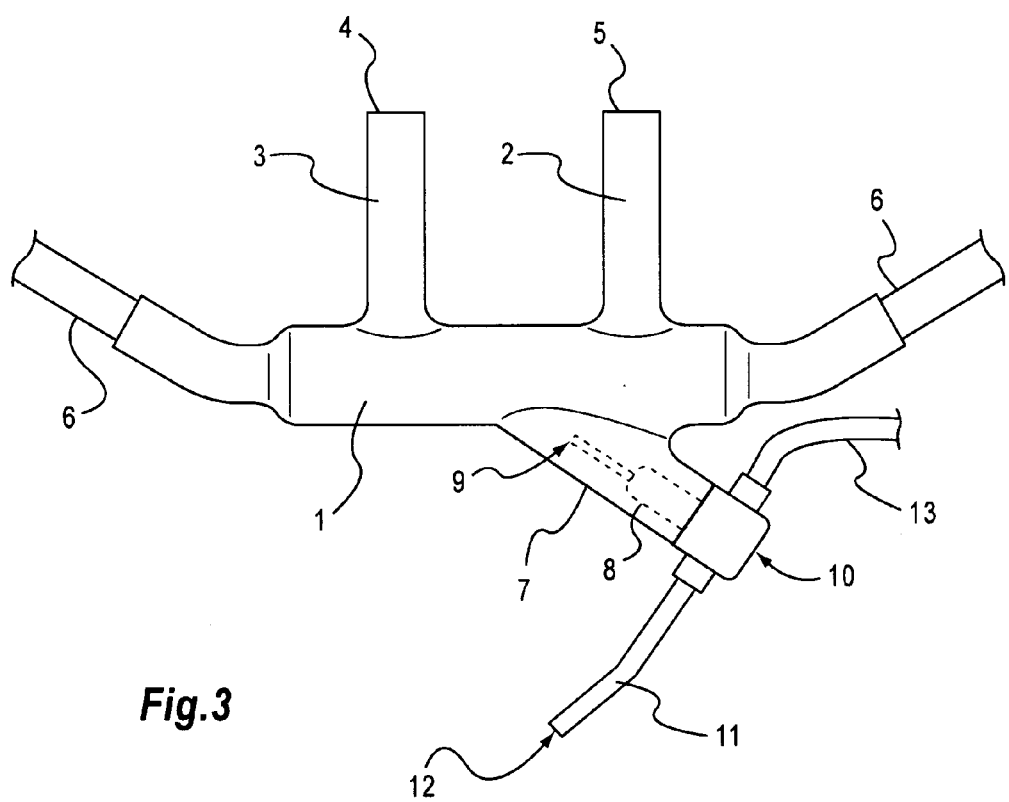
FIG. 3 illustrates a top plan view of the preferred embodiment of the invention including the manifold and two cannula wherein the first temperature sensor of FIG. 2 is inserted into the chamber of the manifold by a port.

FIG. 3 illustrates a top plan view of the preferred embodiment of the invention including the manifold 1 and the two cannulas 2 and 3 wherein the first temperature sensor of FIG. 2 is inserted into the chamber of the manifold through the sensor port 7. The terminus of the sensor terminal 9 is in or nearly in the flow of the nasal breath but is protected by the cylinder of the sensor port 7.

Figure 4:
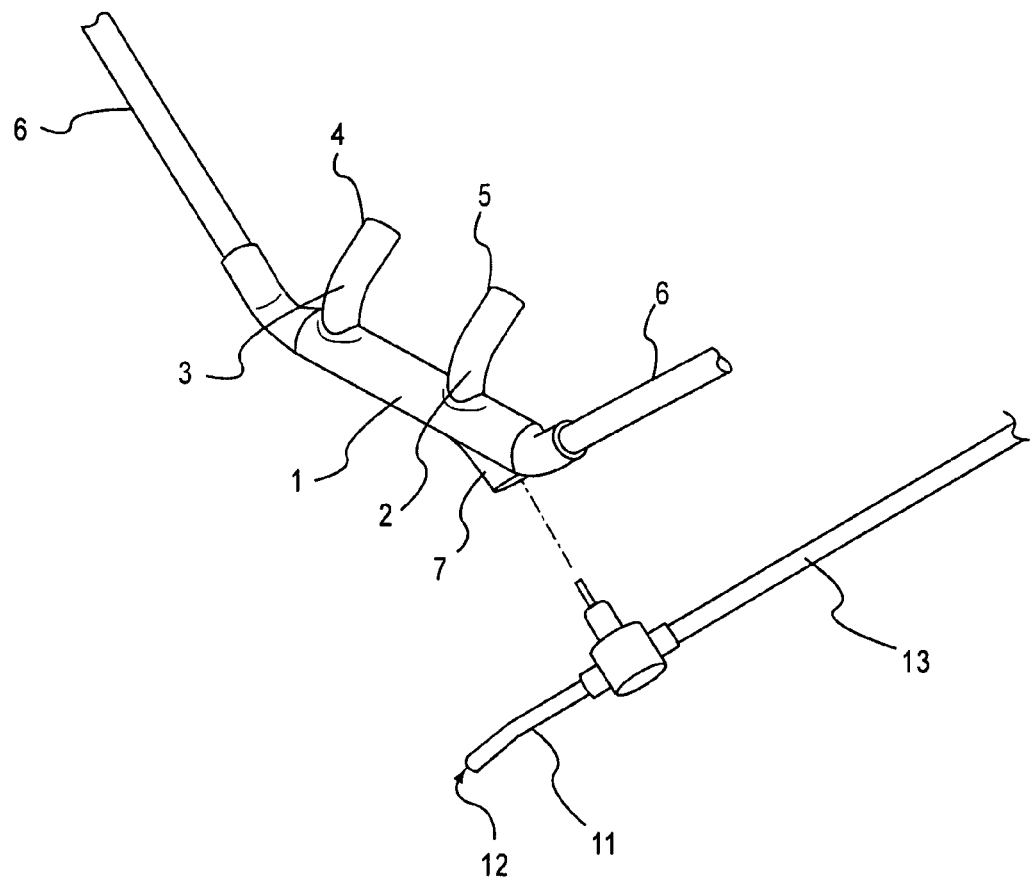
FIG. 4 illustrates a perspective view of the preferred embodiment of the invention including the manifold and two cannula separated from the first temperature sensor of FIG. 2.

FIG. 4 illustrates a perspective view of the preferred embodiment of the invention including the manifold 1 and two cannulas 2 and 3 separated from the first temperature sensor of FIG. 2. This view illustrates the desirable characteristic of the friction fit of the sensor port 7 and the complementary plug 8. The first temperature sensor can be fitted into the sensor port 7 at numerous radial angles so as to place the terminus of the second temperature sensor directly over the patient's mouth.

Figure 5:
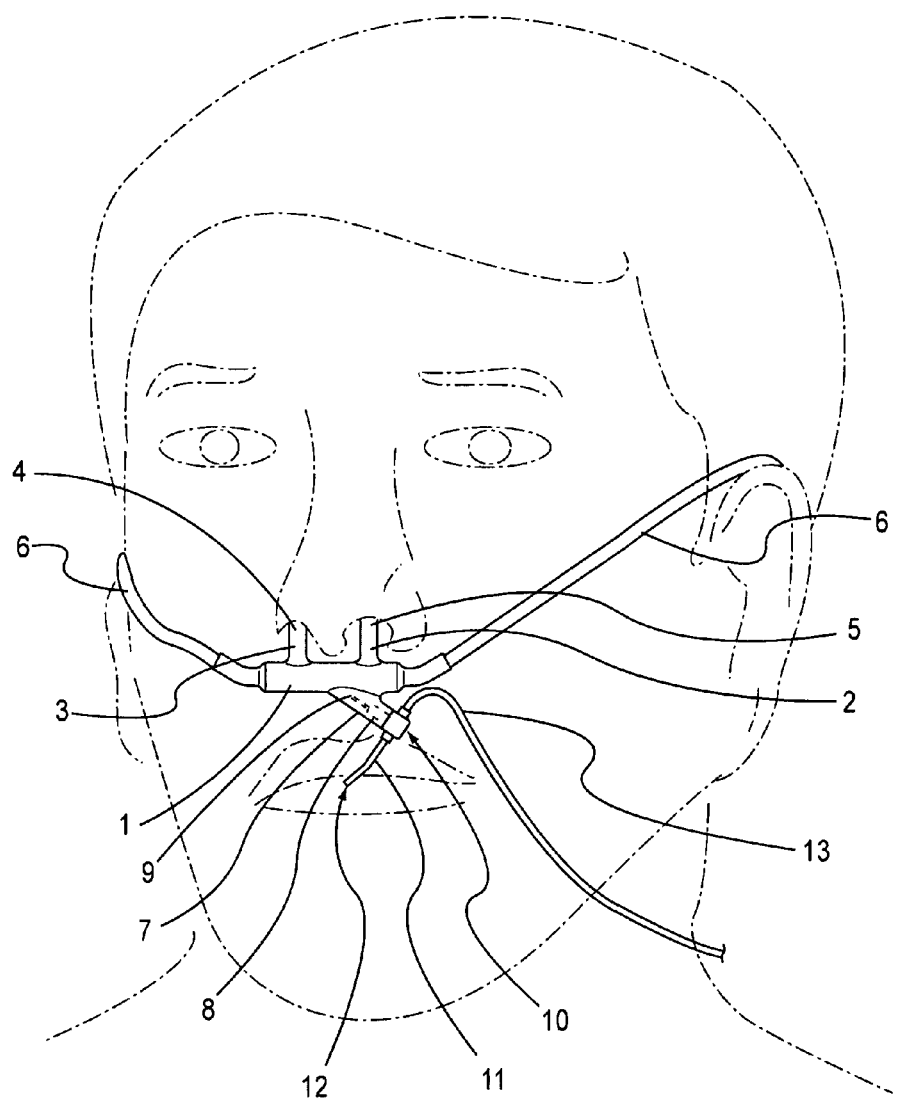
FIG. 5 illustrates a perspective view of the preferred embodiment of the invention on a patient with the manifold and two cannula, the temperature sensor, and a second temperature sensor for sensing oral air flow temperatures.

FIG. 5 illustrates a perspective view of the preferred embodiment of the invention on a patient with the manifold 1 and the two cannulas 2 and 3, the first temperature sensor for nasal air flow temperatures, and a second temperature sensor for sensing oral air flow temperatures. The size, shape, and geometry of the various components can be altered to the integrated thermal and pressure device in comfortable configurations. For example, the preferred embodiment shown in FIG. 5 is suitable for most adults. However, the components can be sized and shaped to fit infants or special needs victims.

The device with two nasal cannulas fits on a patient like any standard cannula with each pressure conducting tube looping over the patient's ears. An added feature is that the lead wire for the thermal sensor can be attached to the device by means of an integrated clip or by tape. In constructing the device, one or more clips can be slipped over a cannula tube before it is glued to the manifold. These clips can enable the sleep technologist to attach the wire to the cannula tube more easily to hold the wire away from the patient's nose area and to prevent the wire from dangling or being pulled or caught on another object.

Figure 6:
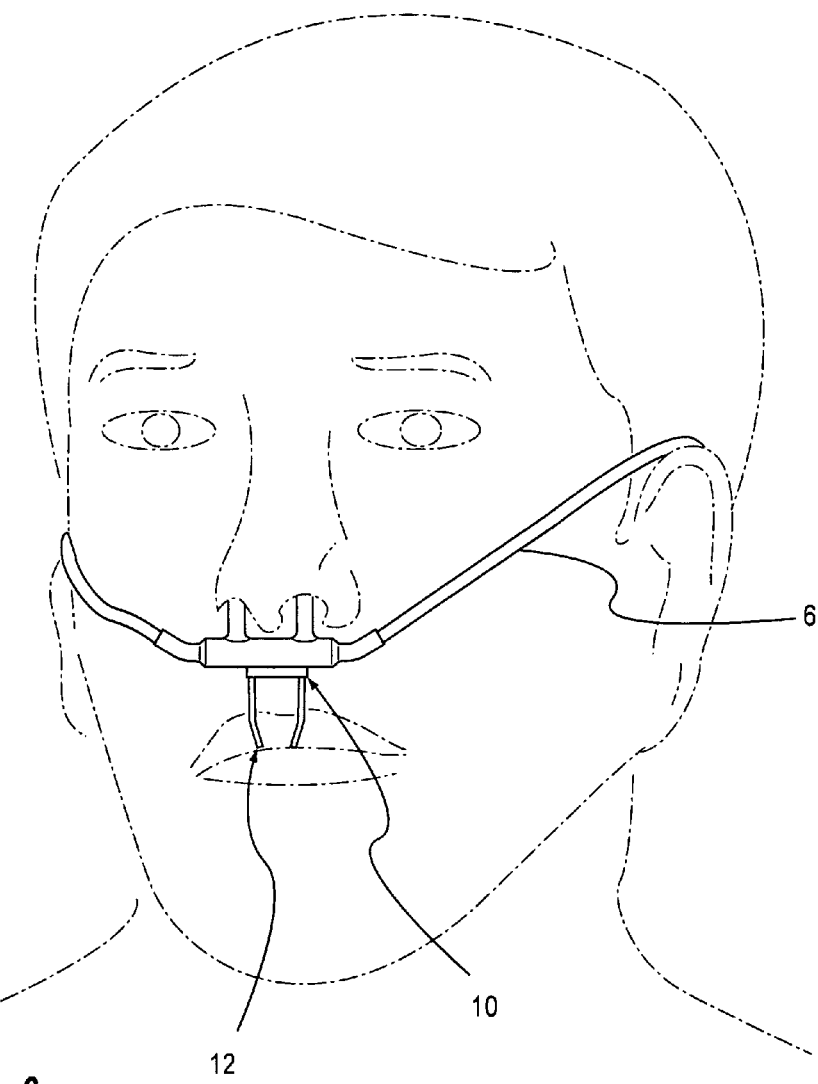
FIG. 6 illustrates a perspective view of an alternative embodiment of the invention on a patient with the manifold and two cannula, the temperature sensor, and a second temperature sensor for sensing oral air flow temperatures.

FIG. 6 illustrates a perspective view of an alternative embodiment of the invention on a patient with the manifold and two cannula, the temperature sensor, and a second temperature sensor for sensing oral air flow temperatures. The junction 10 is a compact shape to hold a two-pronged second thermal sensor 12 for oral temperatures. This embodiment can use a single pressure conducting tube 6 extending from one side of the manifold 1 and an electrical cable from the other side of the manifold 1 for the first temperature sensor (not shown) and the second temperature sensor.

The invention can be attached to a variety of commercially available pressure transducers. Desirable pressure transducers read the changes in air pressure and send a signal through a jack box, processor, or other suitable device to the polysomnographic recorder. The thermal sensors are generally either thermocouples or thermistor assemblies that have wires also leading to the recorder jack box or comparable device.

The first temperature sensor detects temperature changes in nasal airflow, and an optional second temperature sensor can be placed on a flexible wire that can be positioned near the mouth to detect temperature changes in oral airflow. The wire allows for a variety of positioning options to best detect oral airflow temperature.

The invention can also be configured using a sensor port on the top of the manifold for a nasal temperature sensor. In such an embodiment, the terminus of the reusable nasal thermal sensor can enter from the top of the cannula close to the nares of the cannula, and the oral temperature sensor can extend down to a position in front of the patient's mouth.

The sensor port for the nasal temperature or thermal sensor can be on the side of the main chamber of the manifold. The temperature sensor can be attached on the front of the manifold with the terminus of the nasal temperature sensor terminal inserted into the cannula. In this embodiment, the oral temperature sensor can be shorter and still be positioned in front of the patient's mouth. The central location also helps to balance the temperature sensor to the cannula and provides better patient comfort.

Another embodiment is a Y-shaped end on one side of the manifold so that the cannula tube is inserted into one channel of the Y-shaped structure and the reusable temperature sensor is inserted into the other channel. The remaining extension is a single pressure conducting tube similar to a standard cannula.

The invention can also include a divided flow cannula where the nasal and oral airflow is separated. In such an example the main body of the cannula can be configured with two ports. One port is where the nasal temperature sensor or node is inserted on the nasal pressure side of the manifold, and another is where the oral temperature node or sensor can be inserted and held on the oral pressure side of the manifold. The ports can be positioned on the top, bottom, or side as with a standard nasal cannula as described above.

The invention can also utilize a nasal cannula that has a small thin solid protrusion below the manifold. A hole can be placed in the solid protrusion so that the reusable temperature sensor can be inserted. The thermal sensor can be a single U-shaped unit with two plugs, each with a temperature node or sensor. One plug can be inserted into the nasal cannula area and the other can be inserted through the solid protrusion that is in front of the patient's mouth to detect oral temperature.

The sensor configuration with a disposable cannula and a reusable thermal sensor discussed here is more cost effective than a fully disposable device, since the thermal sensor can be cleaned and plugged into a new disposable cannula for the next patient.

A fully disposable sensor can be created using the same principles outlined above. In addition, with a fully disposable sensor, the lead wire can be incorporated into the tubing of the cannula device either as a separate small tube "zipped" or incorporated into the main cannula tube or inserted directly into the cannula tube during assembly.

The lead wires can be connected to completely disposable thermal sensors positioned inside the cannula so that they detect the nasal and/or oral temperatures. In a disposable configuration the port is simply a small hole in the cannula body through which the thermal sensor passes and is then sealed with glue or heat.

In any configurations discussed here, the invention eliminates the need to tape or otherwise secure two separate sensors onto the patient with two lead wires in addition to the tubes for the cannula.

The invention include a method for detecting breathing patterns. The method includes a step of placing two parallel nasal cannulas stemming from a manifold into the nasal passages of a patient. The sensing of nasal temperatures of air flowing from one cannula to the other cannula then occurs. The temperatures are sensed in the manifold between the two parallel nasal cannulas. Then, the sensing occurs of air pressures in the manifold through at least one flexible tube stemming from the manifold in an airtight connection with a pressure transducer apparatus. The sensing of oral air flow temperatures is performed with a second temperature sensor in contact with oral breathing of the patient.

We claim:

1. An integrated thermal and pressure sensing device for detecting nasal and oral breathing patterns comprising:
   a manifold;
   two parallel nasal cannulas stemming from the manifold;
   at least one flexible tube stemming from the manifold for providing an airtight connection with the manifold and a pressure transducer apparatus;
   at least a first temperature sensor for detecting temperatures of air flowing from one cannula to the other cannula; and
   a port in the manifold for removably attaching the first temperature sensor in an airtight connection.

2. The integrated thermal and pressure device of claim 1 wherein the first temperature sensor extends into the manifold between the two parallel nasal cannulas.

3. The integrated thermal and pressure device of claim 1 further comprising at least a second temperature sensor for oral breathing.

4. The integrated thermal and pressure device of claim 1 further comprising a wire attached at one end to a base of the first temperature sensor and a second temperature sensor on an opposite end of the wire in contact with oral breathing.

5. An integrated thermal and pressure device for detecting nasal and oral breathing patterns comprising:
   a manifold;
   two parallel nasal cannulas stemming from the manifold;
   at least one flexible tube stemming from the manifold for providing an airtight connection with the manifold and a pressure transducer apparatus;
   a first temperature sensor for detecting temperatures of air flowing from one cannula to the other cannula, the first temperature sensor extends into the manifold between the two parallel nasal cannulas;
   a port in the manifold for removably attaching the first temperature sensor in an airtight connection; and
   at least a second temperature sensor for oral breathing, the second temperature sensor is attached to a wire, the wire is attached at one end to a base of the first temperature sensor and the second temperature sensor is attached to an opposite end of the wire, the second temperature sensor is in contact with oral breathing.

6. A method for detecting breathing patterns with the integrated thermal and pressure sensing device of claim 1 comprising the steps of:
   placing two parallel nasal cannulas stemming from a manifold into the nasal passages of a patient;
   sensing nasal temperatures of air flowing from one cannula to the other cannula, the temperatures are sensed in the manifold between the two parallel nasal cannulas;
   sensing air pressures in the manifold through at least one flexible tube stemming from the manifold in an airtight connection with a pressure transducer apparatus; and
   sensing oral air flow temperatures with a second temperature sensor in contact with oral breathing of the patient.

* * * * *